United States Patent [19]
Vendittelli

[11] Patent Number: 4,777,834
[45] Date of Patent: Oct. 18, 1988

[54] METHOD FOR DETERMINING A COMPOSITE MATERIAL CONSTITUTING THE MOVING PARTS OF A HERMETICALLY SEALED REFRIGERATING COMPRESSOR AND HERMETICALLY SEALED REFRIGERATING COMPRESSOR COMPRISING THE PARTS DETERMINED BY SAID METHOD

[75] Inventor: Serge Vendittelli, Syssinet, France

[73] Assignee: L'Unite Hermetique, La Verpilliere, France

[21] Appl. No.: 918,060

[22] Filed: Oct. 14, 1986

[30] Foreign Application Priority Data

Oct. 16, 1985 [FR] France ............................. 85 15305

[51] Int. Cl.$^4$ .................... G01N 33/00; G01N 25/00; G01N 17/00; G01M 13/00
[52] U.S. Cl. ..................................... 73/865.6; 374/57; 417/902; 417/DIG. 1
[58] Field of Search .................... 73/865.6, 866, 865.9, 73/866.4; 417/902, DIG. 1; 62/403, 498, DIG. 2; 374/57, 45

[56] References Cited

U.S. PATENT DOCUMENTS

| | | | |
|---|---|---|---|
| 2,188,303 | 1/1943 | Roberts | 73/865.9 X |
| 2,331,099 | 10/1943 | Anderson | 73/865.9 X |
| 2,733,600 | 2/1956 | Sahs et al. | 73/865.9 X |
| 3,772,918 | 11/1973 | Bowles | 73/865.6 |
| 3,839,946 | 10/1974 | Paget | 417/DIG. 1 |
| 3,903,752 | 9/1975 | Riffe | |
| 4,348,206 | 9/1982 | Sandhu | 73/865.6 X |
| 4,436,049 | 3/1984 | Ante et al. | 73/865.6 X |
| 4,462,302 | 7/1984 | Hertell | 92/248 |
| 4,571,093 | 2/1986 | Gottlieb | 73/865.6 X |
| 4,655,235 | 4/1987 | Scott, Jr. | 73/865.6 X |

FOREIGN PATENT DOCUMENTS

| | | | |
|---|---|---|---|
| 2817123 | 3/1979 | Fed. Rep. of Germany | 417/902 |
| 2815471 | 10/1979 | Fed. Rep. of Germany | 417/902 |
| 308227 | 7/1971 | U.S.S.R. | 374/45 |
| 859845 | 8/1981 | U.S.S.R. | 374/45 |

OTHER PUBLICATIONS

"Dupont Teflon Fluorocarbon Resins for Electrical and Electronic Systems"; Dupont Polychemical Dept.; 20 pages; published by May 1961.

*Primary Examiner*—Tom Noland
*Attorney, Agent, or Firm*—Oblon, Fisher, Spivak, McClelland & Maier

[57] ABSTRACT

The invention relates to a method for determining a composite material constitutive of moving parts in a hermetically sealed refrigerating compressor, wherein a composite material, of which the initial mechanical and thermal properties fulfull the conditions corresponding to the mechanical and thermal stresses in compressors, is placed during a first determined test period T1 in an environment containing the chemical products that are present in a compressor, at a test temperature equivalent to the maximal operating temperature of a compressor, and wherein at the end of this period, its chemical and mechanical properties are measured, and compared with the initial mechanical or chemical properties, and it is assessed by calculation what such properties would become once the material would have been used in an environment of a compressor during a second period T2, longer than the first test period T1, and wherein this material is thus utilized for producing parts provided the assessed properties satisfy the required properties after an operating period corresponding to the second period T2.

13 Claims, 1 Drawing Sheet

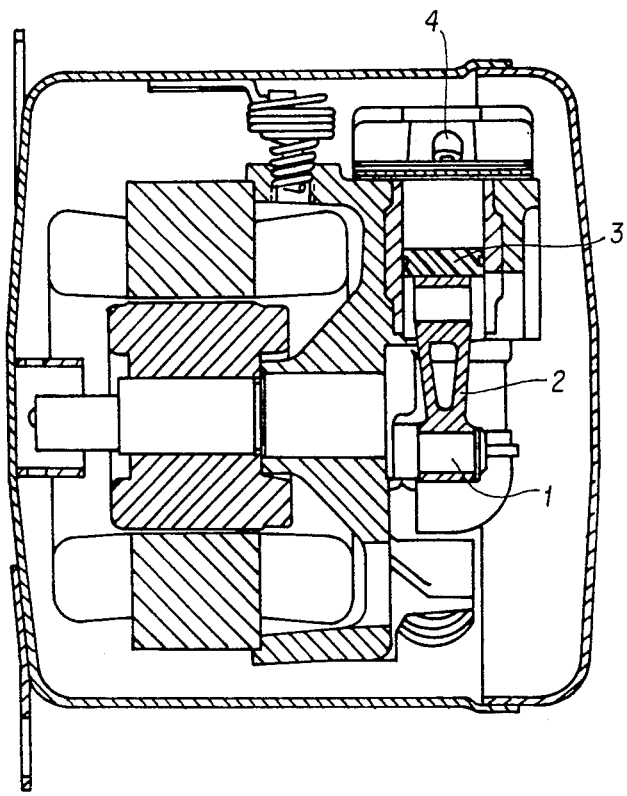

METHOD FOR DETERMINING A COMPOSITE MATERIAL CONSTITUTING THE MOVING PARTS OF A HERMETICALLY SEALED REFRIGERATING COMPRESSOR AND HERMETICALLY SEALED REFRIGERATING COMPRESSOR COMPRISING THE PARTS DETERMINED BY SAID METHOD

BACKGROUND OF THE INVENTION

1. Field of the invention

The invention relates to a method for determining a composite material constitutive of moving parts, such as crankshafts, connecting rods, pistons and valves, of a hermetically sealed refrigerating compressor and a refrigerating compressor comprising such parts made of composite material whose determination has been performed through using the present method.

2. Summary of the prior art

For many years efforts have been made to reduce the mass or weight of moving parts found in refrigerating compressors or units, especially the crankshafts, connecting rods, pistons and valves, since these parts consume a considerable amount of energy with respect to the total amount of energy required for the compression of the refrigerating fluid.

Furthermore, in compressors that comprise an uneven number of pistons, it is necessary to add balancing counter-weights in order to reduce the forces of inertia. These counter-weights have masses that proportionally reduce the efficiency of the compressor.

The reduction of the moving masses leads to a reduction in the power necessary for the motor, thus of the size of the windings and furthermore a reduction of vibrations and noise.

In numerous industrial applications, use is made of composite materials, i.e. synthetic materials mixed with fibrous materials, in order to produce structures having a reduced mass or weight with respect to the former known solutions.

It has thus been envisaged to utilize composite materials during the production of the moving parts of compressors.

However, if in certain applications the use of composite materials raises no particular problem, the same is not true for the production of hermetically sealed refrigerating compressor parts.

Indeed, in the other fields, the choice of materials is most often made in function of their mechanical or thermic properties. Thus, for example, during the production of body parts for a land vehicle, it is of great importance that the various elements be capable of withstanding mechanical stresses to which they are submitted. For the obtention of thermal insulating elements or of elements which contact heated parts, it is of great importance that the elements be capable of withstanding the thermal stresses.

For the production of parts which are intended to be moved inside compressors, the composite material has to be determined as a function of the particular and simultaneous conditions of use.

On the one hand, the moving parts are subjected to high mechanical stresses; on the other hand, the operating temperature is high, in the region of 200° C.; furthermore, the environment in which these elements are located is chemically very corrosive.

The mechanical and physical properties are determined for several temperatures, but in non-corrosive environments. Furthermore, the manufacturers determine the chemical stability of a given composite material in a given environment for several temperatures but without mechanical stresses. Therefore, the only knowledge of properties given by a manufacturer does not allow to determine in advance whether a material is suitable or not for producing the above-mentioned compressor parts.

The invention is based upon these observations and relates to a method for determining a composite material intended to be utilized in the production of parts moving in a hermetically sealed refrigerating compressor, and a hermetically sealed refrigerating compressor comprising the parts determined by this method.

SUMMARY OF THE INVENTION

The invention proposes a method for determining a composite material constitutive of the moving parts in a hermetically sealed refrigerating compressor, wherein a composite material, of which the mechanical and thermal properties initially given for a non-corrosive environment fulfill the conditions corresponding to the mechanical and thermal stresses in a compressor, is placed during a first determined test period T1 in an environment containing the chemical products that are present in a compressor, at a temperature equivalent to the maximal operating temperature of a compressor, and wherein at the end of this period, it is removed from the environment, its chemical and mechanical properties are measured, and wherein through comparison with the initial mechanical or chemical properties, are assessed by calculation any eventual alterations to the mechanical and/or chemical properties once the material will have been used in the environment of a compressor during a second period T2, larger than the first period T1, and wherein this material is thus utilized for producing the said parts provided its assessed properties satisfy the property requirements of a compressor after an operating period corresponding to the period T2.

According to another characteristic, the assessment of the properties is determined for a period T2 which is longer than the lifespan of a compressor, i.e. from 12 to 15 years.

The method according to the invention is therefore particularly advantageous with respect to the methods of the prior art, since after a determined test period, not only are the modifications of the properties of the materials checked, and the materials whose properties have been modified turned aside, but also the properties that these materials will have after a given operating time are assessed even if they have been modified at the end of the test.

BRIEF DESCRIPTION OF THE DRAWING

The FIGURE is a sectional view of a hermetically sealed refrigerating compressor embodying the invention.

Character 1 is a crankshaft, 2 is a connecting rod, 3 is a piston and 4 is a valve. These parts are made of a composite material determined by the disclosed method. The compressor illustrated is otherwise identical to that disclosed in U.S. Pat. No. 3,903,752 by Delmar R. Riffe.

DESCRIPTION OF THE PREFERRED EMBODIMENT

Other advantages, objects and features of the invention will become apparent from the following description, given by way of non-limitative illustration.

A composite material comprises at least two elements: a synthetic material called herein-after connecting matrix, most frequently in the form of a resin, and a fibrous material such as glass fiber, or carbon fiber.

These materials can be transformed, certain through injection, others by compression, according to the nature and/or the rate of the fibers present inside. The fibers can in fact be long, short or in the woven or fabric form.

The aim of the transformation is to produce parts, but said operation does not constitute the object of the present invention.

It is however interesting to note that the properties of a composite material are associated to the rate of fibers, their nature, and the matrix used.

The method according to the invention consists in selecting from among the known composite materials those of which the initial noted mechanical and thermal properties are suitable, in checking through measurement whether these noted properties are correct and satisfy the conditions prevailing in the compressors, then in subjecting them to a test in a medium or environment containing the chemical products present in a compressor at the operating temperature of a compressor. Upon completion of this test, the chemical and mechanical properties are checked.

If the product is exceedingly spoiled chemically, it is turned aside. The product is also turned aside if the mechanical properties upon completion of the test are such that they are totally unsuitable for the environment conditions of a refrigerating compressor.

On the contrary, in the case where the properties of a product upon completion of the test are still satisfactory, they are compared with the initial properties and it is thus determined by calculation how said materials would evolve if the product was utilized in a compressor over a period corresponding to at least the mean lifespan of a compressor, under extreme chemical and thermal conditions.

All the materials that would thus have inadequate mechanical and/or chemical properties are turned aside.

Preferably, if a chemical modification is observed upon completion of the test, the material is turned aside prior to determining the future mechanical properties.

In one example of carrying out the method according to the invention, after having selected the composite materials of which the initial mechanical and thermal properties, given outside the chemically corrosive environment, are suitable, samples are produced in order to subject them to the test.

The chemical test consists in placing the samples in an environment containing compressor lubricating oil and refrigerant fluid, at a temperature corresponding to the maximum operating temperature of the compressors, during a determined period T1.

Preferably, the temperature is about 200° C. In one application, the test lasts 7 days, after which the samples are removed.

Preferably, the tests is carried out in the most corrosive environment that it is possible to develop in a compressor. Therefore, the tests is carried out, for example, in a medium containing naphtenic oils and refrigerant fluids, and it is considered that if the results are satisfactory, they will also be satisfactory for paraffinic oils, since the reacting products that they develop with the refrigerant fluid are less corrosive. Indeed, the paraffinic oils are more indifferent to the chemical agents surrounding them, and in particular to the refrigerant fluid.

Among the numerous known composite materials, there are very few that present the initial mechanical and thermal properties announced and checked as correct and which are thus subjected to the test.

This situation has led to testing materials constituted of impregnated epoxy resin, materials constituted of polyamide and glass, materials constituted of polyester and glass and materials constituted of carbon and glass fibers with ester vinyl resin. All these materials have been turned aside upon completion of the test due to the measured chemical and/or mechanical instability of the resin.

Similarly, other materials have been tested that were constituted of a cetone ethyl polyester based resin, others based on polyamide resin and others based on sulfone polyester resin.

Upon completion of the test, these materials still exhibit good chemical and mechanical properties. The assessment of the future mechanical and chemical properties was thus carried out by calculation for each of these products.

The calculation leads to turn aside cetone ethyl polyester-based materials since they display poor mechanical properties after completion of an operating period corresponding to the period T2 selected by the calculation.

The calculation has led to retaining a material constituted by polyimide resin mixed with 30% of glass fibers which is transformed through injection.

The calculation has led to retaining a material constituted by polyimide resin and 65% of glass fibers, which is transformed by compression.

The calculation has led to retaining a composite material constituted by a glass fiber fabric preimpregnated with polyimide resin and transformed after cutting out through compression and conformation.

The calculation has allowed to retaining a composite material constituted by sulfone polyester resin and 30% of glass fibers that can be transformed through injection.

Another object of the invention is to produce a compressor of which at least one of the moving parts is made of one of the composite materials determined by the method according to the invention, whether it concerns the connecting rods, crankshafts, pistons or valves.

The parts are made through injection or compression, according to the determined composite material.

I claim:

1. Method for determining a composite material constitutive of the moving parts in a hermetically sealed refrigerating compressor, wherein a composite material, of which the mechanical and thermal properties initially given for a non-corrosive environment fulfill the conditions corresponding to the mechanical and thermal stresses in compressors, is placed during a first determined test period T1 in an environment containing the chemical products that are present in a compressor, at a test temperature equivalent to the maximal operating temperature of a compressor, and wherein at the end of this period, the chemical and mechanical properties are measured, and are compared with the initial mechanical or chemical properties, and it is assessed by calculation what such properties would become once the material would have been used in an environment of a compressor during a second period T2, longer than the first test period T1, and wherein this material is thus utilized for producing the said parts provided the assessed properties satisfy the required properties after an operating period corresponding to the second period T2.

2. Method according to claim 1, wherein the test is carried out in a medium containing refrigerant fluid and naphtenic oil.

3. Method according to claim 1, wherein the second period T2 utilized for the assessment is at least equal to the lifespan of a compressor.

4. Process according to claim 3, wherein the second period T2 is about 15 years.

5. Method according to claim 1, wherein the test temperature is about 200° C.

6. Method according to claim 1, wherein the test is performed during a first period T1 of seven days.

7. Method according to claim 1, wherein the assessment of the properties during the second period T2 is only performed if the mechanical and chemical properties measured after completion of the test satisfy the conditions required during the first period T1 in a compressor.

8. Method according to claim 7, wherein the evaluation of the properties after the second period T2 is performed only if the chemical properties have not been modified during the test.

9. Hermetically sealed refrigerating compressor comprising among its moving parts at least a connecting rod, a crankshaft, a piston and valving wherein at least one of these parts is made of a composite material determined by the method according to one of the claims 1 to 8.

10. Hermetically sealed refrigerating compressor according to claim 9, wherein at least one of the said moving parts is made of an injected composite material and constituted by a mixture of a polyimide resin and 30% of glass fibers.

11. Hermetically sealed refrigerating compressor according to claim 9, wherein at least one of the said moving parts is made of a compressed composite material and constituted by a polyimide resin and 65% of glass fibers.

12. Hermetically sealed refrigerating compressor according to claim 9, wherein at least one of the said moving parts is made of a composite material transformed by cutting out, compression and conformation and constituted of a mixture of a fabric of glass fibers and a polyimide resin.

13. Hermetically sealed refrigerating compressor according to claim 9, wherein at least one of the said moving parts is made of an injected composite material and constituted by a mixture of sulfone polyester resin and 30% of glass fibers.

* * * * *